United States Patent
Boutet et al.

(10) Patent No.: US 8,901,291 B2
(45) Date of Patent: Dec. 2, 2014

(54) METHOD FOR CRYSTALLIZATION OF FUCOSE

(75) Inventors: Julien Boutet, La Plaine sur Mer (FR); Gyula Dekany, Sinnamon Park (AU); Ágnes Jànosi, Budapest (HU); Gergely Pipa, Budapest (HU); Ferenc Horvàth, Pilisszentkereszt (HU); Krisztián Kovàcs, Ráckeve (HU); Ignacio Pérez Figueroa, Miami, FL (US); Markus Hederos, Svedala (SE); Andreas Schroven, Barssel (DE); Ioannis Vrasidas, Thessaloniki (GR); Piroska Kovács-Pénzes, Jászberény (HU); Christian Risinger, Rottweil (DE); Sándor Demkò, Debrecen (HU); Lars Kröger, Hamburg (DE); Christoph Röhrig, Mühlingen (DE)

(73) Assignee: Glycom A/S, Kongens Lyngby (DK)

( * ) Notice: Subject to any disclaimer, the term of this patent is extended or adjusted under 35 U.S.C. 154(b) by 163 days.

(21) Appl. No.: 13/698,430

(22) PCT Filed: May 19, 2011

(86) PCT No.: PCT/DK2011/050167
§ 371 (c)(1),
(2), (4) Date: Nov. 16, 2012

(87) PCT Pub. No.: WO2011/144213
PCT Pub. Date: Nov. 24, 2011

(65) Prior Publication Data
US 2013/0072675 A1     Mar. 21, 2013

(30) Foreign Application Priority Data
May 19, 2010   (DK) ................................ 2010 70207

(51) Int. Cl.
*C07H 1/06*     (2006.01)
*C07H 3/02*     (2006.01)
*C07H 3/08*     (2006.01)

(52) U.S. Cl.
CPC .. *C07H 3/02* (2013.01); *C07H 1/06* (2013.01); *C07H 3/08* (2013.01)
USPC ......................................................... 536/127

(58) Field of Classification Search
None
See application file for complete search history.

(56) References Cited

U.S. PATENT DOCUMENTS 7,037,378 B2 *   5/2006   Jumppanen et al. ............ 127/30

FOREIGN PATENT DOCUMENTS

WO         2005040430 A1     5/2005

OTHER PUBLICATIONS

Defaye J., et al., "An efficient synthesis of L-fucose and L-(4-2H)fucose." Carbohydrate Research, Elsevier Science Publishers B.V., Amsterdam, NL, 1984, vol. 126, pp. 165-169, XP002452735.
Hricoviniova Z., "The influence of microwave irradiation on stereospecific Mo(VI)-catalyzed transformation of deoxysugars," Tetrahedron: Asymmetry, Elsevier Ltd., 2009, vol. 20, pp. 1239-1242, XP026210053.
Petrus L., et al., "The Bilik Reaction," Topics in Current Chemistry, Springer-Verlag, Berlin-Heidelberg, 2001, vol. 215, pp. 15-41.
Saari P., et al., "A Novel Chromatographic Production Scale Separation Process for L-Fucose," Journal of Liquid Chromatography & Related Technologies, Taylor & Francis Group, LLC, 2009, vol. 32, pp. 2050-2064.
Vanhooren P.T., et al., "L-Fucose: occurence, physiological role, chemical, enzymatic and microbial synthesis," Journal of Chemical Technology and Biotechnology, Society of Chemistry Industry; 1999, vol. 74, pp. 479-497.

* cited by examiner

*Primary Examiner* — Layla Bland
(74) *Attorney, Agent, or Firm* — McHale & Slavin, P.A.

(57) ABSTRACT

The present application discloses a method for the crystallization of fucose, characterized in that the crystallization is carried out from a mixture comprising fucose and at least one 6-deoxy sugar selected from 6-deoxy-talose and 6-deoxy-gulose. In one embodiment, the mixture comprises fucose and 6-deoxy-talose.

11 Claims, No Drawings

METHOD FOR CRYSTALLIZATION OF FUCOSE

CROSS-REFERENCE TO RELATED APPLICATIONS

This application is a §371 national stage entry of International Application No. PCT/DK2011/050167, filed May 19, 2011, which claims priority to Danish Patent Application No. PA 2010-70207 filed May 19, 2010, the entire contents of which are incorporated herein by reference.

FIELD OF THE INVENTION

The present invention relates to separation of monosaccharides, namely crystallization and separation of fucose from related monosaccharides, especially from its epimer(s).

BACKGROUND OF THE INVENTION

Fucose (6-deoxy-galactose) is one of the examples of so-called rare monosaccharides. Fucose is found in a wide variety of natural products from many different sources, in both D-form and L-form. Fucose occurs in several human milk oligosaccharides, in eggs of sea urchins and in frog spawn. L-Fucose is present in polysaccharides from plants such as seaweed (in the form of fucoidan, sulphated fucose polymer), gum tragacanth, potato, kiwi fruit, soybean, winged bean varieties, canola, etc. In plant material, fucose is typically associated with plant polysaccharides, which are often highly branched structures having L-fucopyranosyl units either at the ends of or within the polysaccharide chains. Both N-and O-glycosyl chains of human or animal glycoproteins may contain L-fucose bound to the termini of the carbohydrate chains. Furthermore, extracellular polysaccharides from various bacteria, fungi and micro-algae also contain L-fucose.

Interest in L-fucose has recently increased because of its potential in the medical field in treating various disease conditions, such as tumors, inflammatory conditions and disorders relating to the human immune system. L-fucose has also applications in the cosmetic field, for instance as skin moisturizing, skin regenerating and anti-aging agent or for prevention epidermal (skin) inflammation.

Although enzyme- or microbe-assisted production of fucose is known from the art, L-fucose is usually obtained from natural sources or produced via chemical modifications of common monosaccharides (see a review on L-fucose: P. T. Vanhooren et al. *J. Chem. Technol. Biotechnol.* 74, 479 (1999) and references cited therein).

Regarding fucose production from natural sources, fucose containing oligosaccharides that can be isolated from biomass, preferably from algae e.g. by extraction, are hydrolyzed to provide a complex mixture containing fucose as well as related sugars and/or derivatives thereof. Recovery of fucose from the mixture typically needs sophisticated separation techniques such as treatment or chromatography with anion or cation exchange resins, dialysis, fractional crystallization, etc., depending on the nature of the accompanying sugars or sugar-related compounds. For example the article of P. Saari et. al. (*J. Liquid Chrom. Rel. Tech.* 32, 2050 (2009)) and the international application WO 2005/040430 disclose chromatographic separation of spent liquor obtained from pulping processes by means of cation and/or anion exchange resins or combination thereof. The resulting syrup, which is enriched in fucose (at least 72%) and still contains rhamnose, methyl α-D-xylopyranoside, xylose, arabinose and galactose as well, was then subjected to fractional crystallization from aqueous ethanol to obtain fucose.

With regard to chemical synthesis of L-fucose, chemical modifications of common monosaccharides like L-galactose, D-galactose, L-arabinose, D-glucose, D-mannose and L-rhamnose have been published. One of the most elegant processes (J. Defaye et al. *Carbohydr. Res.* 126, 165 (1984), Scheme 1., R=Me) starts from L-rhamnose which was first converted to methyl rhamnoside (A) then protected as 2,3-O-isopropylidene acetal (B).

Scheme 1.

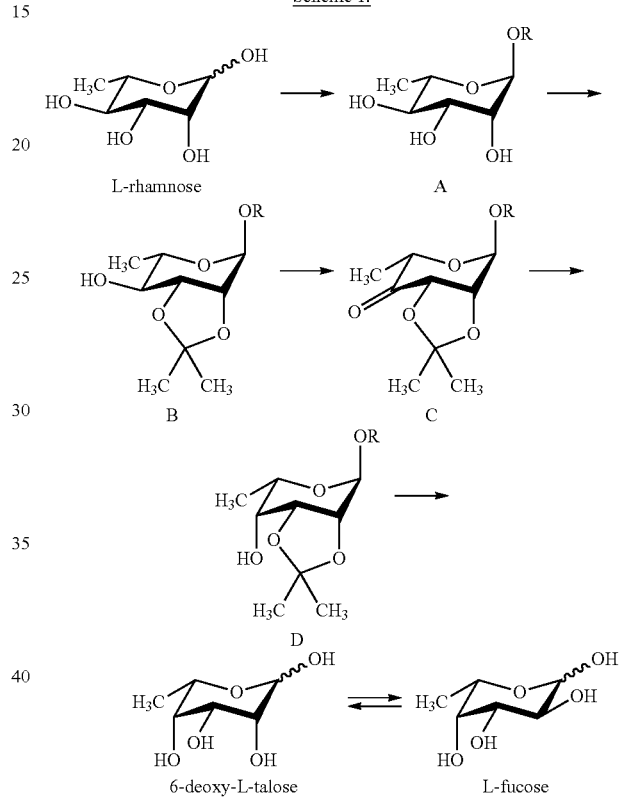

The free 4-OH group was oxidized resulting in the corresponding hexulose (C) followed by borohydride reduction and acidic hydrolysis giving rise to 6-deoxy-L-talose. Epimerization of the latter in the presence of molybdic acid, known as Bílik reaction (see L. Petruš et al. *Topics Curr. Chem.* 215, 15 (2001) and references cited therein), resulted in an equilibrium between 6-deoxy-L-talose and its 2-epimer L-fucose wherein L-fucose was favoured (7:1). As L-fucose forms weaker complex with cations than 6-deoxy-L-talose, separation of these sugars could be effected by means of column chromatography with a cation exchange resin in Ca- or Ba-form. The same interconversion could be performed under microwave irradiation instead of conventional conductive heating and the epimers were separated on a column filled with DOWEX 50W X8 in Ba-form (Z. Hricovíniová *Tetrahedron: Asymmetry* 20, 1239 (2009)).

The main drawback of the above-mentioned procedures is the unavoidable chromatographic separation in order either to get the pure substance or to obtain at least a mixture that is enriched in the target compound but still contains undesired derivatives. Although repeated chromatographic separation may result in the improvement of the purity, its high cost and relatively long technological time to handle the feed solution and the column packing, to carry out the separation and optionally to regenerate the packing, especially in large or industrial scale, can be disadvantageous and/or cumbersome.

Crystallization or recrystallization is one of the simplest and cheapest methods to isolate a product from a reaction mixture, separate it from contaminations and obtain pure substance. Isolation or purification that uses crystallization makes the whole technological process robust and cost-effective, thus it is advantageous and attractive compared to other procedures.

BRIEF DESCRIPTION OF THE INVENTION

The present application provides a method for the crystallization of fucose, characterized in that the crystallization is carried out from a mixture comprising fucose and at least one 6-deoxy sugar selected from 6-deoxy-talose and 6-deoxy-gulose. In a preferred embodiment the mixture comprises fucose and 6-deoxy-talose.

Furthermore, the present application provides a method for the crystallization of fucose, characterized in that the crystallization is carried out from a mixture comprising fucose and isobutanol.

DETAILED DESCRIPTION OF THE INVENTION

The inventors of the present application discovered that fucose can be crystallized from a mixture comprising fucose and at least one 6-deoxy sugar selected from 6-deoxy-talose and 6-deoxy-gulose, preferably 6-deoxy-talose. Crystallization replaces chromatography with cation exchange resin suggested by the art thus makes it attractive for large or industrial scale production of fucose. The claimed method provides fucose of high purity in one crystallization step, typically crystallization of batches of at least 1 kg of fucose, such as at least 5 kg, or at least 50 kg, or even at least 200 kg, e.g. at least 1 ton of fucose.

The crystallization is typically carried out by dissolving the mixture comprising fucose and at least one 6-deoxy sugar selected from 6-deoxy-talose and 6-deoxy-gulose in a solvent or mixture of solvents at elevated temperature to give warm or hot saturated or nearly saturated solution, which is then allowed to cool under or without stirring. Upon cooling the fucose crystallizes out from the solution, seed crystals of fucose may facilitate the crystallization.

In one embodiment a mixture comprising fucose and 6-deoxy-talose is dissolved in a solvent or mixture of solvents at elevated temperature to give warm or hot saturated or nearly saturated solution, which is then allowed to cool under or without stirring. Upon cooling the fucose crystallizes out from the solution, seed crystals of fucose may facilitate the crystallization.

In a preferred embodiment fucose is L-fucose and 6-deoxy-talose is 6-deoxy-L-talose.

In another preferred embodiment fucose is L-fucose and 6-deoxy-gulose is 6-deoxy-L-gulose.

According to another preferred realization of the invention the crystallization is carried out from a solution comprising one or more $C_1$-$C_6$ alcohol as the solvent. "$C_1$-$C_6$ alcohol" refers to a mono- or dihydroxy alcohol having 1 to 6 carbon atoms such as methanol, ethanol, n-propanol, i-propanol (i.e. isopropanol), n-butanol, i-butanol (i.e. isobutanol), s-butanol, t-butanol, amylalcohol, n-hexanol, ethylene glycol, propylene glycol, etc. Preferably monohydroxy alcohol(s) is/are used as solvent, more preferably $C_1$-$C_4$ alcohol(s) such as methanol, ethanol, n-propanol, i-propanol, n-butanol, i-butanol, s-butanol or t-butanol. Even more preferably a $C_3$-alcohol (n-propanol or i-propanol) or a $C_4$-alcohol (n-butanol, i-butanol, s-butanol or t-butanol) is the choice of solvent, particularly i-butanol.

In another embodiment the solvent system used for crystallization contains one or more $C_1$-$C_6$ alcohol, preferably one or more $C_1$-$C_6$ monohydroxy alcohol. More preferably the solvent is one $C_1$-$C_4$ alcohol such as methanol, ethanol, n-propanol, i-propanol, n-butanol, i-butanol, s-butanol or t-butanol. Even more preferably a $C_3$-alcohol (n-propanol or i-propanol) or a $C_4$-alcohol (n-butanol, i-butanol, s-butanol or t-butanol) is the choice of solvent, particularly i-butanol.

According to another realization the solvent system may contain water. The water content typically ranges from 0.1 v/v % to 15 v/v %, preferably 2 v/v % to 10 v/v %.

In one embodiment, the solvent system consists of from 85 v/v % to 100 v/v %, such as from 90 v/v % to 100 v/v % or from 90 v/v % to 99.9 v/v % or from 90 v/v % to 98 v/v %, of a $C_3$-$C_4$ monohydroxy alcohol and from 0 v/v % to 15 v/v %, such as from 0 v/v % to 10 v/v % or from 0.1 v/v % to 10 v/v % or from 2 v/v % to 10 v/v %, of water.

The crude material from which fucose is crystallized contains at least 50%, preferably at least 60%, more preferably at least 70% of fucose based on weight of the dried material. The combined amount of fucose with 6-deoxy-talose and/or 6-deoxy-gulose typically ranges from 65% to 95%. In one embodiment, the combined amount of fucose and 6-deoxy-talose ranges from 65% to 95%. The ratio of fucose compared to 6-deoxy-talose and/or 6-deoxy-gulose may be about 1:1, preferably more than 6:4, in particular more than 7:3. Particularly, the fucose/6-deoxy-talose ratio in the solution to be crystallized may be about 1:1, preferably more than 6:4, in particular more than 7:3.

In another preferred embodiment the concentration of fucose and at least one 6-deoxy sugar selected from 6-deoxy-talose and 6-deoxy-gulose to be crystallized is more than 0.1 g/ml, preferably 0.2-0.3 g/ml with respect to the combined amount of fucose and at least one 6-deoxy sugar selected from 6-deoxy-talose and 6-deoxy-gulose. Particularly, the concentration of fucose/6-deoxy-talose solution to be crystallized is more than 0.1 g/ml, preferably 0.2-0.3 g/ml with respect to the combined amount of fucose and 6-deoxy-talose.

In one typical embodiment of the invention, the solution containing fucose and at least one 6-deoxy sugar selected from 6-deoxy-talose and 6-deoxy-gulose is heated above 50° C., preferably to reflux and allowed to cool to the temperature of at the most 25° C., for example to 0-25° C. Crystals precipitated are collected by filtration and dried to give rise to pure fucose. Particularly, the solution containing fucose and 6-deoxy-talose is heated above 50° C., preferably to reflux and allowed to cool to the temperature of at the most 25° C., for example to 0-25° C. Crystals precipitated are collected by filtration and dried to give rise to pure fucose.

According to a further preferred embodiment the crude material comprising fucose accompanied by 6-deoxy-talose and/or 6-deoxy-gulose to be crystallized is obtained from the epimerization reaction of crude or purified 6-deoxy-talose in the presence of Mo(VI). When 6-deoxy-talose is taken as a crude material, it may contain rhamnose which transforms into 6-deoxy-gulose under the condition used. The epimerization is typically takes place in hot water above 75-80° C. (if conductive heating is applied), preferably at reflux, until an equilibrium is reached (6-12 hours, can be checked by HPLC). In case of microwave irradiation significantly less time (5-15 min) is enough to arrive at equilibrium. The Mo(VI)-containing catalyst used for epimerization might be either homogeneous or heterogeneous. Among homogeneous catalysts $MoO_3$, "white" molybdic acid ($MoO_3.H_2O$) or "yellow" molybdic acid ($MoO_3.2H_2O$) are of particular relevance, all of them are soluble in water under the conditions of the Bílik reaction resulting a low pH ($\approx$2.9) of the solution, which is an optimum value for the epimerization. Any molybdate or polymolybdate salt (e.g. ammonium heptamolybdate, ammonium dimolybdate, sodium molybdate, etc.) can also be used for the epimerization, optionally in combination with mineral acids to ensure optimum pH. Immobilized (poly) molybdate compounds bound to anion exchange resins as heterogeneous catalysts can also be applied successfully. After reaching the equilibrium the catalyst is removed by neutralization with an anion exchange resin and filtration to give a fucose/(6-deoxy-talose and/or 6-deoxy-gulose) mixture in water. The water is then evaporated, optionally co-evaporated with solvent(s) capable to remove water from a solution such as ethanol, isopropanol, isobutanol, toluene, etc. yielding the crude fucose with 6-deoxy-talose and/or 6-deoxy-gulose ready for crystallization.

Particularly, the fucose/6-deoxy-talose mixture to be crystallized is obtained from the epimerization reaction of 6-deoxy-talose in the presence of Mo(VI).

6-Deoxy-talose applied in the Bílik epimerization can be produced by known methodologies (e.g. from L-rhamnose see J. Defaye et al. *Carbohydr. Res.* 126, 165 (1984))., Scheme 1, R=$C_1$-$C_4$-alkyl). As none of intermediates of the reaction sequence has been purified, the reaction mixture after Bílik epimerization may contain any of them in max. 3%, respectively.

6-Deoxy-talose remained in the mother liquor after crystallization can be recycled. According to one methodology the mother liquor itself or combined with 6-deoxy-talose of different source can be reprocessed to a new cycle of epimerization (see above). According to another method 6-deoxy-talose and fucose of the mother liquor obtained from crystallization are separated (Scheme 2). The mother liquor was concentrated and treated with acetone or dimethoxy-propane in the presence of an acid to form a mixture of 1,2:3,4-di-O-isopropylidene-α-fucopyranoside (E) and 2,3-O-isopropylidene-6-deoxy-talose (F). After neutralization and removing the solvent the mixture was dissolved in water and the apolar diisopropylidene-fucose derivative was extracted to hexane, while the more polar talose derivative remained in the aqueous phase. The phases were separated, both phases were concentrated by evaporation separately and the crude materials were treated with acid to remove the protective groups to get fucose and 6-deoxy-talose, respectively. Both monosaccharides can be crystallized from appropriate solvent(s). 6-Deoxy-talose thus obtained can then be used in a new cycle of epimerization.

Scheme 2. (L-series depicted)

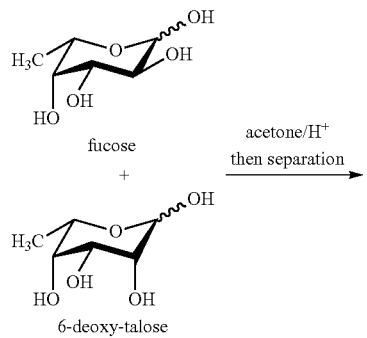

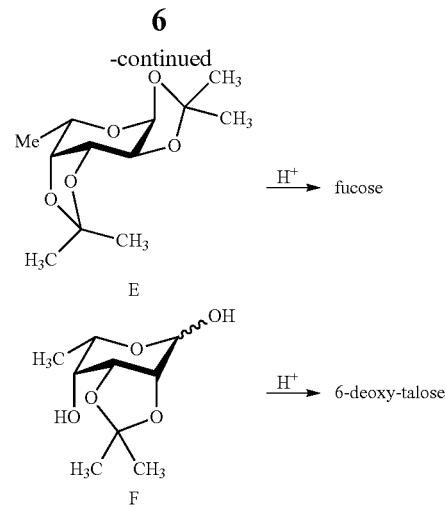

The inventors of the present application also discovered that fucose can be crystallized from a mixture comprising fucose and isobutanol as the solvent. Crystallization replaces chromatography with cation exchange resin suggested by the art thus makes it attractive for large or industrial scale production of fucose.

The mixture to be crystallized may further contain one or more monosaccharide, preferably at least one 6-deoxy sugar selected from 6-deoxy-talose and 6-deoxy-gulose, preferably 6-deoxy-talose.

The crystallization is typically carried out by providing a warm or hot, saturated or nearly saturated solution comprising fucose and isobutanol, which is then allowed to cool under or without stirring. Upon cooling the fucose crystallizes out from the solution, seed crystals of fucose may facilitate the crystallization.

In one embodiment a mixture comprising fucose and 6-deoxy-talose is dissolved in isobutanol at elevated temperature to give warm or hot saturated or nearly saturated solution, which is then allowed to cool under or without stirring. Upon cooling the fucose crystallizes out from the solution, seed crystals of fucose may facilitate the crystallization.

In a preferred embodiment fucose is L-fucose, 6-deoxy-talose (if present) is 6-deoxy-L-talose and 6-deoxy-gulose (if present) is 6-deoxy-L-gulose.

According to another realization isobutanol may contain water. The water content typically ranges from 0.1 v/v % to 15 v/v %, preferably 2 v/v % to 10 v/v %.

The crude material from which fucose is crystallized contains at least 50%, preferably at least 60%, more preferably at least 70% of fucose based on weight of the dried material. The combined amount of fucose with 6-deoxy-talose and/or 6-deoxy-gulose ranges from 65% to 95%. The ratio of fucose compared to 6-deoxy-talose and/or 6-deoxy-gulose may be about 1:1, preferably more than 6:4, in particular more than 7:3. Particularly, the fucose/6-deoxy-talose ratio in the solution to be crystallized may be about 1:1, preferably more than 6:4, in particular more than 7:3.

In another preferred embodiment the concentration of fucose and at least one 6-deoxy sugar selected from 6-deoxy-talose and 6-deoxy-gulose to be crystallized is more than 0.1 g/ml, preferably 0.2-0.3 g/ml with respect to the combined amount of fucose at least one 6-deoxy sugar selected from 6-deoxy-talose and 6-deoxy-gulose. Particularly, the concentration of fucose/6-deoxy-talose solution to be crystallized is more than 0.1 g/ml, preferably 0.2-0.3 g/ml with respect to the combined amount of fucose and 6-deoxy-talose.

In one typical embodiment of the invention, the solution comprising fucose, isobutanol and at least one 6-deoxy sugar selected from 6-deoxy-talose and 6-deoxy-gulose is heated above 50° C., preferably to reflux and allowed to cool to the temperature of at the most 25° C., for example to 0-25° C. Crystals precipitated are collected by filtration and dried to give rise to pure fucose. Particularly, the solution containing fucose and 6-deoxy-talose in isobutanol is heated above 50° C., preferably to reflux and allowed to cool to the temperature of at the most 25° C., for example to 0-25° C. Crystals precipitated are collected by filtration and dried to give rise to pure fucose.

The mixture comprising fucose and 6-deoxy-talose to be crystallized is obtained from the epimerization reaction of 6-deoxy-talose in the presence of Mo(VI). When 6-deoxy-talose is taken as a crude material, it may contain rhamnose which transforms into 6-deoxy-gulose under the condition used. The epimerization is typically takes place in hot water above 75-80° C. (if conductive heating is applied), preferably at reflux, until an equilibrium is reached (6-12 hours, can be checked by HPLC). In case of microwave irradiation significantly less time (5-15 min) is enough to arrive at equilibrium. The Mo(VI)-containing catalyst used for epimerization might be either homogeneous or heterogeneous. Among homogeneous catalysts $MoO_3$, "white" molybdic acid ($MoO_3.H_2O$) or "yellow" molybdic acid ($MoO_3.2H_2O$) are of particular relevance, all of them are soluble in water under the conditions of the Bílik reaction resulting a low pH (≈2.9) of the solution, which is an optimum value for the epimerization. Any molybdate or polymolybdate salt (e.g. ammonium heptamolybdate, ammonium dimolybdate, sodium molybdate, etc.) can also be used for the epimerization, optionally in combination with mineral acids to ensure optimum pH. Immobilized (poly)molybdate compounds bound to anion exchange resins as heterogeneous catalysts can also be applied successfully. After reaching the equilibrium the catalyst is removed by neutralization with an anion exchange resin and filtration to give a fucose/(6-deoxy-talose and/or 6-deoxy-gulose) mixture in water. The water is then evaporated, optionally co-evaporated with solvent(s) capable to remove water from a solution such as ethanol, isopropanol, isobutanol, toluene, etc. yielding the crude fucose with 6-deoxy-talose and/or 6-deoxy-gulose ready for crystallization.

6-Deoxy-talose remained in the mother liquor after crystallization can be recycled. According to one methodology the mother liquor itself or combined with 6-deoxy-talose of different source can be reprocessed to a new cycle of epimerization (see above). According to another method 6-deoxy-talose and fucose of the mother liquor obtained from crystallization are separated (Scheme 2). The mother liquor was concentrated and treated with acetone or dimethoxy-propane in the presence of an acid to form a mixture of 1,2:3,4-di-O-isopropylidene-α-fucopyranoside (E) and 2,3-O-isopropylidene-6-deoxy-talose (F). After neutralization and removing the solvent the mixture was dissolved in water and the apolar diisopropylidene-fucose derivative was extracted to hexane, while the more polar talose derivative remained in the aqueous phase. The phases were separated, both phases were concentrated by evaporation separately and the crude materials were treated with acid to remove the protective groups to get fucose and 6-deoxy-talose, respectively. Both monosaccharides can be crystallized from appropriate solvent(s). 6-Deoxy-talose thus obtained can then be used in a new cycle of epimerization.

Other features of the invention will become apparent in the course of the following descriptions of exemplary embodiments which are given for illustration of the invention and are not to be limiting thereof.

EXAMPLES

Example 1

$MoO_3$ (600 mg) was added to a mixture of 6-deoxy-L-talose (100 g) in water (1.5 l). The reaction mixture was stirred for 9.5 h at reflux. At 80° C. resin IRA-67 (SUPELCO, 50 g) was added and the mixture was stirred for further 30 min, filtered and distilled off. The residue was dissolved in isopropanol (400 ml) and directly evaporated. Isobutanol (400 ml) was then added and the mixture was heated under reflux for 10 min and allowed to cool. Crystallization spontaneously occurs or it was promoted by adding seed crystals. After one night at room temperature the suspension was filtered to give L-fucose (52 g, 52%).

The mother liquor was concentrated, the residue (~50 g) was dissolved in acetone and p-toluenesulphonic acid (5.1 g) was added portion wise at rt. The mixture was stirred overnight at rt, then neutralized with triethylamine (4 ml) and concentrated in vacuo. The residue was dissolved in water (70 ml) and the aqueous phase was extracted with hexane (2×100 ml and 1×50 ml). The aqueous phase was reserved for further treatment (see below). The combined hexane phase was washed with water (30 ml), dried on $MgSO_4$, filtered and concentrated to dryness. Water (20 ml) and IR-120 resin (3 g) were added and the mixture was stirred overnight at reflux. The resin was filtered off and washed with a solution of triethylamine in DCM (2 ml in 100 ml). The aqueous phase was extracted, washed with DCM (3×100 ml) and distilled off. The residue was dissolved in isopropanol and directly evaporated. Isobutanol (40 ml) was then added and the mixture was heated under reflux (110° C.) for 10 min and allowed to cool. Crystallization spontaneously occurs or it was promoted by adding seed crystals. After one night at room temperature the suspension was filtered to give L-fucose (5.6 g, 6%).

The aqueous phase reserved (see above) was extracted with dichloromethane (2×200 ml and 3×100 ml), the combined organic phase dried on $MgSO_4$, filtered and concentrated to dryness. Water (50 ml) and IR-120 resin (5 g) were added and the mixture was stirred for 2 h at reflux. The resin was filtered off and washed with a solution of triethylamine in DCM (10 ml in 200 ml). The aqueous phase was extracted, washed with DCM (2×100 ml) and distilled off. The residue was dissolved in isopropanol (75 ml), evaporated and isopropanol was again added (75 ml). The mixture was heated under reflux for 10 min and allowed to cool. Crystallization spontaneously occurs or it was promoted by adding seed crystals. After one night at room temperature the suspension was filtered to give 6-deoxy-L-talose (9.2 g, 9.2%).

Example 2

Into a 500 ml Erlenmeyer flask were placed 50 g of sodium molybdate and 200 ml of deionized water. The mixture was stirred until a solution was obtained, then the pH was adjusted to 1 by the careful addition of concentrated sulfuric acid (10 ml). To the acidic molybdate solution were then added 50 g of IRA-400 resin (OH form, Supelco). The agitation was stopped and the suspension was kept at room temperature for two days, with occasional gentle swirling. The resulting solid catalyst was collected on a glass frit funnel. In order to completely remove all unexchanged molybdate, the solid catalyst was washed with portions of deionized water.

The resin-supported molybdate obtained above (10 g) was added to a mixture of 6-deoxy-L-talose (10 g) in water (40 ml). The reaction mixture was stirred at 78° C. (inside the reactor). After cooling to rt the mixture was filtered, the filtrate passed through a column of IRA 400 resin (5 g, OH form, d=1 cm, l=5 cm) two times and concentrated. The residue was dissolved in isopropanol (40 ml) and directly evaporated. Isobutanol (50 ml) was added and the mixture was heated to reflux for 10 min. and allowed to cool. Crystallization spontaneously occurs or it was promoted by adding seed crystals. After 6 h at room temperature the suspension was filtered to give L-fucose (5.4 g, 54%).

The invention claimed is:

1. A method for the crystallization of fucose, the method comprising the step of crystallizing fucose from a mixture comprising fucose and at least one 6-deoxy sugar selected from 6-deoxy-talose and 6-deoxy-gulose, wherein the step of crystallizing fucose is carried out using one or more $C_1$-$C_6$ alcohols as the solvent(s), said solvent(s) comprising at least a $C_3$-alcohol or a $C_4$ alcohol.

2. The method according to claim 1, wherein fucose is L-fucose, 6-deoxy-talose is 6-deoxy-L-talose and 6-deoxy-gulose is 6-deoxy-L-gulose.

3. The method according to claim 1, wherein the step of crystallizing fucose is carried out using a solution having a concentration more than 0.1 mg/ml with respect to the combined amount of fucose and at least one 6-deoxy sugar selected from 6-deoxy-talose and 6-deoxy-gulose.

4. The method according to claim 1, wherein the step of crystallizing fucose is carried out using a solution having a concentration more than 0.1 mg/ml with respect to the combined amount of fucose and 6-deoxy-talose.

5. The method according to claim 1, wherein the method comprises the steps of heating the mixture to a temperature above 50° C. and subsequently allowing the mixture to cool to a temperature of at the most 25° C.

6. The method according to claim 1, wherein the step of crystallizing fucose is carried out using i-butanol as the solvent, and wherein the solution is first warmed to reflux and subsequently allowed to cool down to 25° C.

7. The method according to claim 1, wherein the method comprises the step of epimerizing 6-deoxy-talose in the presence of Mo(VI) so as to obtain said mixture comprising fucose and at least one 6-deoxy sugar selected from 6-deoxy-talose and 6-deoxy-gulose.

8. The method according to claim 7, wherein 6-deoxy-L-talose is subjected to epimerization in the presence of Mo(VI) in the form of $MoO_3$.

9. The method according to claim 7, wherein 6-deoxy-L-talose is obtained from L-rhamnose.

10. The method according to claim 1, wherein the method comprises the further step of recycling the mother liquor of the crystallization comprising fucose and 6-deoxy-talose is recycled.

11. The method according to claim 1, wherein the step of crystallizing fucose is carried out using one or more $C_1$-$C_6$-alcohols as the solvent(s), said solvent(s) comprising at least i-butanol.

* * * * *